United States Patent
Reinhardt et al.

(10) Patent No.: US 6,822,113 B2
(45) Date of Patent: Nov. 23, 2004

(54) PROCESS FOR PREPARING ACYLOXYBENZENESULFONATES

(75) Inventors: Gerd Reinhardt, Kelkheim (DE); Peter Naumann, Taunusstein (DE); Alexander Lerch, Gelnhausen (DE); Wolf-Dieter Mueller, Charlotte, NC (US); Narayan D. Sadanani, Charlotte, NC (US)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/431,951

(22) Filed: May 8, 2003

(65) Prior Publication Data

US 2004/0019229 A1 Jan. 29, 2004

(30) Foreign Application Priority Data

Jul. 25, 2002 (DE) .......................... 102 33 827

(51) Int. Cl.$^7$ .............................................. C07C 69/00
(52) U.S. Cl. .......................................... 560/142; 562/56
(58) Field of Search .......................... 560/142; 562/46, 562/56, 30, 45

(56) References Cited

U.S. PATENT DOCUMENTS

| | | | |
|---|---|---|---|
| 3,503,888 A | 3/1970 | Miller et al. ................ 252/117 |
| 4,587,054 A * | 5/1986 | Hardy et al. ................ 260/410 |
| 4,666,636 A | 5/1987 | Shen ....................... 260/512 R |
| 5,069,828 A | 12/1991 | Dumas et al. .............. 260/402 |
| 5,523,434 A * | 6/1996 | Burns et al. ................. 554/68 |
| 6,448,430 B1 * | 9/2002 | Hembre ....................... 560/98 |
| 2002/0058824 A1 | 5/2002 | Majerczak et al. ......... 549/438 |

FOREIGN PATENT DOCUMENTS

| | | |
|---|---|---|
| EP | 0 098 129 | 1/1984 |
| EP | 0 105 672 | 4/1984 |
| EP | 0 105 673 | 4/1984 |
| EP | 0 125 641 | 11/1984 |
| EP | 0 164 786 | 12/1985 |
| EP | 0 220 826 | 5/1987 |
| WO | WO 01/19771 | 3/2001 |

* cited by examiner

*Primary Examiner*—Rita Desai
*Assistant Examiner*—Robert Shiao
(74) *Attorney, Agent, or Firm*—Richard P. Silverman

(57) ABSTRACT

A process for preparing acyloxybenzenesulfonates by reacting anhydrous phenolsulfonates with carboxylic acid derivatives comprises conducting the reaction with a salt of a phenolsulfonic acid which has a water content of less than 0.5% by weight and has been contacted with a substance having basic properties.

7 Claims, No Drawings

PROCESS FOR PREPARING ACYLOXYBENZENESULFONATES

The invention relates to a process for preparing acyloxybenzenesulfonates starting from carboxylic acid derivatives and low water content salts of a phenolsulfonic acid.

Acyloxybenzenesulfoninc acids and their salts are long-established compounds. Depending on the chain length of the acyl group they may find use as surfactants, as bleach activators, or in other applications.

DE 666 626 describes their surfactant properties and their general use in laundry detergents, while compounds having from 6 to 12 carbon atoms in the alkyl chain, in combination with persalts, are claimed as bleaches by EP 98 129, EP 105 672, EP 105 673 and EP 125 641.

For the preparation of acyloxybenzenesulfonic acids and their salts a multiplicity of methods have been described. They can be obtained by heating a mixture of trifluoroacetic anhydride, sodium phenolsulfonate (SPS), and a ($C_6$–$C_{19}$) alkane-carboxylic acid. According to U.S. Pat. No. 4,587,054 this reaction can also be carried out in two stages: first, the alkanecarboxylic acid is converted into the anhydride in the presence of an excess of acetic anhydride, and then the isolated anhydride is reacted with dry phenolsulfonate. This reaction takes place at temperatures from 180 to 220° C. under base catalysis. The acid catalyzed reaction of a relatively long-chain alkanoic anhydride with SPS in an aprotic solvent is claimed in U.S. Pat. No. 4,588,532; the acid catalysis (toluenesulfonic acid and related compounds) allows a reaction regime at just 120° C.

Also known from the literature is the transesterification of ($C_2$–$C_3$)acyloxy-benzenesulfonate with a ($C_6$–$C_8$) alkanecarboxylic acid accompanied by removal of the short-chain alkanecarboxylic acid formed. It is also possible to react alkali metal or alkaline earth metal phenolsulfonates with a $C_2$–$C_{31}$-alkanephenyl ester at from 200 to 350° C.

A further preparation variant is the reaction of aliphatic or aromatic carbonyl halides with salts of phenolsulfonic acid. The reaction can be carried out under Schotten-Baumann conditions in an aqueous system (U.S. Pat. No. 5,523,434), but in that case leads only to moderate conversions. More advantageous is the reaction of anhydrous salts of phenolsulfonic acids in water-free media. Organic solvents such as methylene chloride (U.S. Pat. No. 3,503,888), high-boiling hydrocarbons (EP 220 826), xylene or toluene (EP 164 786), and trifluoroacetic acid (WO 01/19 771) serve as the reaction medium. According to U.S. Pat. No. 5,069,828 this reaction is conducted in an aprotic organic solvent in the presence of a phase transfer catalyst. According to U.S. patent application Ser. No. 20 020 058 824 this reaction can also be conducted solventlessly if an excess of acid chloride is employed.

With all of the known industrially useful processes the problem arises that it is necessary to use virtually anhydrous SPS for the reaction since otherwise the carboxylic acid derivative (halide or anhydride) and the finished ester undergo hydrolysis in the presence of traces of water, leading to considerable losses of yield. Virtually anhydrous means, in this case, water contents <0.5% by weight, preferably <0.2% by weight.

SPS is available commercially as the dihydrate, with a water fraction of approximately 15% by weight. By conventional drying the water content can be lowered to about 2% by weight. According to U.S. Pat. No. 5,069,828 it is possible to remove the residual water by azeotropic distillation in the presence of an azeotrope former such as xylene. Because of the massive amount of time required, however, this is not very rational on the industrial scale or in plants which operate continuously.

As is known from U.S. Pat. No. 4,666,636, the water content can be reduced to less than 0.5% by weight by means of special drying in corresponding apparatus. For this purpose, however, it is necessary to stick rigidly to defined drying conditions (170 to 200° C., inert gas, vacuum, fluidized bed drier, thorough mixing). If these conditions are not observed precisely, SPS enters into a number of secondary reactions, as a result of which the product is irreversibly damaged. The consequence of this is that both the degree of conversion in the following acylation and the color of the end product are significantly adversely affected. Incorrect drying, i.e., excessively long residence times or excessively high temperatures, lead to overdrying of the SPS, which in the acylation reaction leads to degrees of conversion of less than 50%. Nor is it possible to improve this by using the acylating component in a superstoichiometric amount. In the industrial operation of SPS drying, however, these specific physical parameters are difficult to observe precisely. It would be useful to find ways of suppressing the disruptive secondary reactions during drying, in order to free the quality of the SPS product from its dependency on drying time, drying temperature, and other physical parameters.

It is an object of the present invention, therefore, to develop a process which can be carried out both industrially and continuously and which allows optimal drying of the SPS, even outside of the reaction conditions specified in U.S. Pat. No. 4,666,636, without tolerating loss of reactivity of the SPS in the downstream acylation stage. The process should at the same time be independent of the physical drying parameters of the sodium phenolsulfonate employed.

It has surprisingly now been found that starting from anhydrous SPS it is possible to prepare acyloxybenzenesulfonates, irrespective of the thermal pretreatment of the SPS employed, if the anhydrous SPS, after its preparation and isolation but before reaction with the carboxylic acid derivative, is contacted with at least one substance having basic properties. Irrespective of physical drying parameters, this SPS then reacts with acylating agents in excellent yields to give acyloxybenzenesulfonates of outstanding quality.

The invention provides a process for preparing acyloxybenzenesulfonates by reacting anhydrous phenolsulfonates with carboxylic acid derivatives, which comprises contacting the salt of a phenolsulfonic acid, after its isolation but before the acylation, with at least one substance having basic properties.

The phenolsulfonate starting compounds used are preferably compounds of the formula

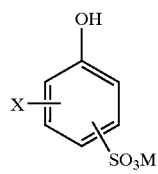

where X is hydrogen, halogen or $C_1$–$C_4$-alkyl and M is an alkali metal or alkaline earth metal ion. Preference is given to sodium ortho- or para-phenolsulfonates, especially sodium para-phenolsulfonate (SPS), which as a result of its preparation process may contain isomeric byproducts (up to 10%) or other impurities in small amounts.

SPS is prepared by sulfonating phenol and then neutralizing the product. Since Na p-phenolsulfonate is of low solubility in water, it can be isolated from the reaction medium by filtration, centrifugation or similar operations. The crude SPS is then washed and after isolation has a high purity and a water content of from 15 to 30%. For the reaction according to the invention with a carboxylic acid derivative it is necessary to dry the phenolsulfonate to a residual moisture content of <0.5%, preferably <0.2%, by weight. This operation can be carried out continuously or in stages via the dihydrate (water content approximately 15% by weight) and quarter-hydrate (water content approximately 2% by weight). Drying can take place in accordance with conventional methods which are known per se, in a disk drier or fluid-bed drier, for example, which allows drying to a residual moisture content of less than 0.1% by weight. In the course of drying it is advantageous to operate under a stream of inert gas. Drying can be operated under reduced pressure or with the same result under atmospheric pressure as well.

Depending on the equipment used the drying times can be between 1 min and 18 h, the temperatures between 80 and 250° C. For the process of the invention the thermal pretreatment of the dried SPS has no effect on the yield of the acylation reaction and it is possible on average to obtain conversions of more than 95%. In particular it is also possible to employ drying conditions which lie outside of the optimal drying conditions specified in U.S. Pat. No. 4,666,636, i.e., conditions which lead to "overdried" product. According to the prior art, such a product cannot be used for acylation reactions since it is not reactive enough.

Suitable substances having basic properties include all organic or inorganic compounds which dissociate in aqueous solution to form hydroxide ions. Use is made in particular of inorganic bases, such as alkali metal or alkaline earth metal oxides, hydroxides, carbonates, hydrogen carbonates, phosphates, etc. Particular preference is given to sodium carbonate, sodium hydrogen carbonate, and sodium hydroxide, but also to the corresponding K salts.

The bases can be contacted either in anhydrous form, i.e., as powders, slurries or pastes, or as an aqueous solution with the SPS. This can be done directly after the SPS has been isolated, i.e., after the filter cake has been washed, or before or during drying to give the dihydrate or quarter-hydrate. Alternatively, contacting may also take place during subsequent drying to give the anhydrous SPS. The addition may be made both in suitable apparatus, such as mixers, or else directly before or during the drying itself. In this specific case this is done most advantageously either by spraying the dissolved base directly into the drying apparatus or by feeding it continuously in parallel with the moist SPS during the charging of the drier.

The amount of base needed is between 0.01 and 10% by weight, preferably from 0.1 to 5% by weight, based on the SPS in dihydrate form (water content approximately 15% by weight).

As carboxylic acid derivatives it is possible to use both the halides and the anhydrides of the formula

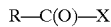

where X=Cl, Br, O—C(O)—R, where R can be $C_1$–$C_{18}$ linear or branched alkyl radicals, the alkyl group being uninterrupted or interrupted, if desired, by an ester group or amide group, or $C_5$–$C_{11}$ aryl radicals, containing, if desired, heteroatoms such as nitrogen and being unsubstituted or substituted.

As carboxylic acid it is possible to use linear or branched, saturated or unsaturated alkanecarboxylic acids having from 1 to 22 carbon atoms. Examples thereof are acetic acid, hexanoic acid, heptanoic acid, octanoic acid, methyloctanoic acid, nonanoic acid, 3,3,5-isononanoic acid, decanoic acid, undecanoic acid, undecenoic acid, lauric acid, myristic acid, hydrogenated tallow fatty acid, stearic acid, benzoic acid or chlorobenzoic acid. Particular preference is given to octanoic acid, nonanoic acid, isononanoic acid, decanoic acid, and lauric acid. The alkanecarboxylic acid may bear further substituents such as halogens, nitro groups or amino groups or may be interrupted by oxygen atoms, ester functions and/or amido functions. Examples thereof are n-octylchloroformic acid, nonylchloroformic acid, octanoyloxyacetal chloride, phthalimidohexanoyl chloride and nonanoylamidohexanoyl chloride.

Particularly suitable are the carbonyl chlorides or bromides, the chlorides being preferred. They may be prepared from the corresponding carboxylic acids, for example, by reaction with phosgene, thionyl chloride, phosphorus trichloride, phosphorus oxychloride, phosphorus pentachloride or phosphorus tribromide.

The anhydrides used may be symmetric or unsymmetric compounds. Examples thereof are acetic anhydride, nonanoic anhydride, isononanoic anhydride, benzoic anhydride, octanoic anhydride or acetylnonanoic anhydride.

Carboxylic acid derivative and phenolsulfonate can be reacted, in accordance with the invention, preferably in a molar ratio of from 0.8:1 to 2:1, preferably from 1:1 to 1.5:1, with one another.

The acylation may be conducted in common protic or aprotic solvents or in an excess of the corresponding acid. Particularly preferred as reaction medium are aliphatic or aromatic hydrocarbons having boiling points of between 80 and 200° C., in particular from 100 to 180° C., examples being toluene, xylene, paraffins having from 8 to 22 carbon atoms, such as decane, undecane, dodecane, hexadecane or octadecane, or mixtures thereof. Particularly suitable are aliphatic hydrocarbon mixtures such as are available commercially as Shellsols (Shell), ISOPAR G and ISOPAR 4 (ESSO). The solubility of the SPS in this reaction medium is frequently below 1%.

An additional catalyst is normally not necessary but may offer advantages in certain cases. Preference is given to open-chain or cyclic tertiary amines or carboxamides (as described in DE 101 29 663.5), phase transfer catalysts or acidic catalysts such as p-toluenesulfonic acid. The molar ratio of the catalyst used to the phenolsulfonate is from 0.0001:1 to 0.02:1, preferably from 0.005:1 to 0.012:1.

The acylation reaction is conducted at temperatures between 60 and 200° C., in particular between 100 and 150° C. The gas formed during the reaction is taken off; if desired, the reaction is blanketed with an inert stream of nitrogen or argon gas. The reaction is conducted as a heterogeneous reaction (slurry), since neither the phenolsulfonate nor the acyloxybenzenesulfonate product have any notable solubility in the reaction medium. The reaction time is guided by the reaction conditions and may amount to between 10 min and 5 h, preferably from 30 to 120 min.

In one particular embodiment the reaction of the invention can be conducted continuously. Particularly suitable for this purpose are tank cascades and/or tubular reactors, such as are known to the skilled worker.

After the end of reaction, the reaction product is isolated by conventional separation methods. Centrifuges and filter apparatus are suitable for this purpose. For complete separation of the catalyst it is advisable to wash the solid reaction product with the reaction medium one or more times. The mother liquor can be used without further purification for the subsequent reactions, or cycled. The acyloxybenzenesulfonate formed is obtained in high yields in the form of a white powder that can be isolated by conventional drying.

The acyloxybenzenesulfonate recovered in this way can be used as a surfactant or persalt activator in laundry and other detergents such as powderous heavy duty laundry detergents, scouring salts or powderous machine dishwasher detergents. In order to increase the storage stability in these formulations it can be converted into a granular form, as the skilled worker is aware.

EXAMPLES

Example 1 (Comparative Example)

Preparation of SPS Filter Cake

Sodium para-phenolsulfonate dihydrate was prepared by neutralizing a solution of phenol sulfonic acid. The product was isolated by filtration and washed with water. This gave a filter cake (SPS filter cake) consisting of white crystals with the following composition >98% sodium p-phenolsulfonate, <2% sodium o-phenolsulfonate, <0.5% sodium 2,4-disulfonate, and <0.5% sulfones.

Example 2

Preparation of Anhydrous SPS (in Accordance With U.S. Pat. No. 4,666,636)

The product was dried at 120° C. and then had a water content of from 2 to 2.5% (quarter-hydrate). The remaining water was then removed in accordance with U.S. Pat. No. 4,666,636, Example 4 (30 min., 180° C.). This gave SPS having a water content of approximately 0.2%.

Use of Anhydrous SPS

Synthesis of Sodium Nonanoyloxybenzenesulfonate 98.1 g (0.5 mol) of dried sodium phenolsulfonate prepared in accordance with Example 2a) were introduced in 150 g of ISOPAR G and this initial charge was heated to 120° C. Thereafter 114.8 g (0.65 mol) of nonanoyl chloride were added dropwise over the course of 30 minutes, followed by stirring at 130° C. The HCl gas formed was taken off. After 2 h the reaction mixture was cooled to 80° C. and filtered. The white reaction product was washed twice with a little ISOPAR G and then dried overnight in a drying oven at 110–130° C.

Crude yield: 164.9 g (yield 98%) of white powder having a sodium nonanoyloxy-benzenesulfonate (NOBS) content of 98.5%. Yield of NOBS: 96%

Example 3 (Comparative Example)

Preparation of Anhydrous SPS (Outside of U.S. Pat. No. 4,666,636)

SPS filter cake was prepared as in Example 1 and then dried at 120° C. to give the quarter-hydrate. The product was subsequently dried at 180° C. for 12 h and had a water content of 0.1%.

Use of Anhydrous SPS

Synthesis of Sodium Nonanoyloxybenzenesulfonate 98.1 g (0.5 mol) of dried sodium phenolsulfonate prepared in accordance with Example 3a) were introduced in 150 g of ISOPAR G and this initial charge was heated to 120° C. Thereafter 114.8 g (0.65 mol) of nonanoyl chloride were added dropwise over the course of 30 minutes, followed by stirring at 120° C. The HCl gas formed was taken off. After 2 h the reaction mixture was cooled to 80° C. and filtered. The gray reaction product was washed twice with a little ISOPAR G and then dried overnight in a drying oven at from 110 to 130° C.

Crude yield: 129.0 g (yield 77%) of beige-brown powder having a sodium nonanoyloxy-benzenesulfonate (NOBS) content of 58%. Yield of NOBS: 44%

Example 4

Preparation of Anhydrous SPS

SPS filter cake was prepared as in Example 1, then washed with 0.05 N sodium hydrogen carbonate solution and subsequently dried at 120° C. to give the quarter-hydrate. The product was subsequently dried at 180° C. for 12 h and then had a water content of 0.2%.

Use of Anhydrous SPS

Synthesis of Sodium Nonanoyloxybenzenesulfonate 98.1 g (0.5 mol) of dried sodium phenolsulfonate prepared in accordance with Example 4a) were introduced in 150 g of ISOPAR G and this initial charge was heated to 120° C. Thereafter 114.8 g (0.65 mol) of nonanoyl chloride were added dropwise over the course of 30 minutes, followed by stirring at 130° C. The HCl gas formed was taken off. After 2 h the reaction mixture was cooled to 80° C. and filtered. The white reaction product was washed twice with a little ISOPAR G and then dried overnight in a drying oven at from 110 to 130° C.

Crude yield: 164.8 g (yield 99%) of white powder having a sodium nonanoyloxy-benzenesulfonate (NOBS) content of 98%. Yield of NOBS: 97%

Example 5

Preparation of Anhydrous SPS

Sodium p-phenolsulfonate filter cake was prepared as in Example 1, adjusted to a pH 7 with 5% sodium carbonate solution and subsequently dried at 120° C. to give the quarter-hydrate. The product was subsequently dried at 180° C. for 12 h and then had a water content of 0.15%.

Use of Anhydrous SPS

Synthesis of Sodium Nonanoyloxybenzenesulfonate

The SPS prepared in accordance with Example 5a) was acylated with nonanoyl chloride as in Example 4b)

Crude yield: 164.8 g (yield 98%) of white powder having a sodium nonanoyloxy-benzenesulfonate (NOBS) content of 98%. Yield of NOBS: 96%

Example 6

Preparation of Anhydrous SPS

Sodium p-phenolsulfonate filter cake was prepared as in Example 1, washed with a 0.2 N sodium dihydrogen phosphate solution, adjusted to a pH 6.9 and subsequently dried at 120° C. to give the quarter-hydrate. The product was subsequently dried at 180° C. for 12 h and then had a water content of 0.25%.

Use of Anhydrous SPS

Synthesis of Sodium Nonanoyloxybenzenesulfonate

The SPS prepared in accordance with Example 6a) was acylated with nonanoyl chloride as in Example 4b)

Crude yield: 162.1 g (yield 96%) of white powder having a sodium nonanoyloxy-benzenesulfonate (NOBS) content of 98%. Yield of NOBS: 94%

Example 7

Preparation of Anhydrous SPS

Sodium p-phenolsulfonate filter cake was prepared as in Example 1, and then dried at 120° C. to give the quarter-hydrate. Thereafter, 2% of a 10% strength NaHCO$_3$ solution was sprayed on, after which the residual water was removed at 180° C. over the course of 12 h. The product then had a water content of 0.18%.

Use of Anhydrous SPS

Synthesis of Sodium Lauroyloxybenzenesulfonate 98.1 g (0.5 mol) of dried sodium phenolsulfonate prepared in accordance with Example 7a) were introduced in 150 g of ISOPAR G and this initial charge was heated to 120° C. Thereafter 142 g (0.65 mol) of lauroyl chloride were added dropwise over the course of 30 minutes, followed by stirring at 130° C. The HCl gas formed was taken off. After 2 h the reaction mixture was cooled to 80° C. and filtered. The white reaction product was washed twice with a little ISOPAR G and then dried overnight in a drying oven at from 110 to 130° C.

Crude yield: 185.5 g (yield 98%) of white powder having a sodium lauroyloxy-benzenesulfonate (LOBS) content of 98%. Yield of LOBS:96%

Example 8

Preparation of Anhydrous SPS

Sodium p-phenolsulfonate filter cake was prepared as in Example 1, and then dried at 120° C. to give the quarter-hydrate. The quarter hydrate was subsequently mixed with 2% of finely ground NaHCO$_3$ and then the product was dried at 180° C. for 12 h. The SPS then had a water content of 0.15%.

Use of Anhydrous SPS

Preparation of Sodium 2-Methyloctanoyloxybenzenesulfonate 98.1 g (0.5 mol) of dried sodium phenolsulfonate prepared in accordance with Example 8a) were introduced in 150 g of ISOPAR G and this initial charge was heated to 120° C. Thereafter 114.7 g (0.65 mol) of 2-methyloctanoyl chloride were added dropwise over the course of 30 minutes, followed by stirring at 120° C. The HCl gas formed was taken off. After 2 h the reaction mixture was cooled to 80° C. and filtered. The white reaction product was washed twice with a little ISOPAR G and then dried overnight in a drying oven at from 110 to 130° C.

Crude yield: 160.9 g (yield 95.7%) of white powder having a sodium methyloctanoyloxybenzenesulfonate content of 95%.

Example 9

Preparation of Anhydrous SPS

Sodium p-phenolsulfonate filter cake was prepared as in Example 1 and then 1.5% of 0.1 N NaHCO$_3$ solution were added, after which the filter cake was dried at 120° C. to give the quarter-hydrate. The product was subsequently dried at 180° C. for 12 h, after which it had a water content of 0.2%.

Use of Anhydrous SPS

Preparation of Nonanoylamidocaproyloxybenzenesulfonic Acid Sodium Salt 135.7 g (0.5 mol) of n-nonanoylamidohexanoic acid were melted at 90° C., 59.5 g (0.5 mol) of thionyl chloride were added dropwise over 2 h, and the reaction mixture was stirred subsequently for 1 h and degassed. The resultant n-nonanoylamido-hexanoyl chloride and 100.1 g (0.5 mol) of anhydrous SPS from Example 9a), in suspension in 300 ml of n-butyl acetate, were added over the course of 5 minutes and the mixture was subsequently stirred at 90° C. for 30 minutes under N$_2$.

After cooling to 30° C., 900 ml of water were added with stirring. 123 g of sodium hydroxide solution (32% strength) were added dropwise at from 35 to 40° C. to set a pH of 8.0. The reaction mixture was cooled to room temperature and the product was filtered off with suction and dried under reduced pressure. This gave an 88% yield of white crystals of n-nonanoylamidocaproyloxybenzenesulfonic acid sodium salt.

The same results, i.e., yields of more than 90% of acyloxybenzenesulfonate, are also obtained when the SPS is dried with removal of the residual water at 220° C. for 30 minutes. This shows that the process of the invention allows very much greater latitude in the drying of the SPS in terms of time and temperature than the process according to U.S. Pat. No. 4,666,636. As a result, the process of the invention can be performed very much more effectively on the industrial scale.

What is claimed is:

1. A process for preparing acyloxybenzenesulfonates comprising reacting an anhydrous salt of phenolsulfonic acid of the formula:

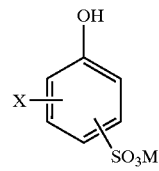

where X is hydrogen, halogen or C$_1$–C$_4$-alkyl and M is an alkali metal or alkaline earth metal ion with a carboxylic acid derivative selected from the group consisting of halides, anhydrides, and mixtures thereof of the formula

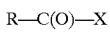

where X=Cl, Br, O—C(O)—R, where R is a C$_1$–C$_{18}$ linear or branched alkyl radical, the alkyl group being uninterrupted or interrupted, by an ester group or amide group, or C$_5$–C$_{11}$ aryl radicals, or C$_5$–C$_{11}$ aryl radicals containing heteroatoms including nitrogen and being unsubstituted or substituted, wherein said anhydrous salt of phenolsulfonic acid has a water content of less than 0.5% by weight and has been contacted before said reacting step with a substance having basic properties which comprises a compound which dissociates in aqueous solution to form hydroxide ions, said substance having basic properties being selected from the group consisting of alkali metal oxides, alkaline earth metal oxides, hydroxides, carbonates, hydrogen carbonates, phosphates, and mixtures thereof, or said substance having basic properties being a sodium or potassium compound selected from the group consisting of carbonate, hydrogen carbonate, hydroxide, and mixtures thereof.

2. The process as claimed in claim 1, wherein said anhydrous salt of the phenolsulfonic acid has a water content of less than 0.2% by weight.

3. The process as claimed in claim 1, wherein from 0.01 to 10% by weight of substance having basic properties is used, based on phenolsulfonate in the form of the dihydrate.

4. The process as claimed in claim 1, wherein said substance having basic properties is used in the form of a powder, slurry, paste or aqueous solution.

5. The process as claimed in claim 1, wherein said anhydrous salt of the phenolsulfonic acid is contacted directly following its isolation with the substance having basic properties.

6. The process as claimed in claim 1, wherein said anhydrous salt of the phenolsulfonic acid is contacted during its drying with the substance having basic properties.

7. The process of claim 1, wherein said process is a continuous process.

* * * * *